United States Patent [19]

Ikeda et al.

[11] 4,003,815
[45] Jan. 18, 1977

[54] APPARATUS FOR MEASURING STRAY CURRENT ELECTROLYTIC CORROSION

[75] Inventors: Hironosuke Ikeda, Hirakata; Makoto Yamada, Katano; Hiroshi Kutsuyama, Hirakata, all of Japan

[73] Assignee: Sanyo Electric Co., Ltd., Osaka, Japan

[22] Filed: May 9, 1975

[21] Appl. No.: 575,998

Related U.S. Application Data

[63] Continuation of Ser. No. 448,285, March 5, 1974, abandoned.

[52] U.S. Cl. .............. 204/195 C; 324/29; 324/71 R; 324/72; 324/76 A
[51] Int. Cl.$^2$ .................. G01N 27/46; G01N 27/42
[58] Field of Search .......... 204/1 C, 19 SC; 324/29, 324/71 R, 72, 72 S, 76 A

[56] References Cited

UNITED STATES PATENTS

| | | | |
|---|---|---|---|
| 2,782,370 | 2/1957 | Ver Nooy | 324/72 |
| 2,803,797 | 8/1957 | Cowles | 324/29 |
| 2,862,177 | 11/1958 | Titterington | 324/29 |
| 2,943,027 | 6/1960 | Schaschl et al. | 204/1 C |
| 2,974,276 | 3/1961 | Davis | 324/29 |
| 2,980,854 | 4/1961 | En Dean et al. | 324/72 |
| 3,064,127 | 11/1962 | Green et al. | 324/72 X |
| 3,189,819 | 6/1965 | Schmidt | 324/72 |
| 3,735,249 | 5/1973 | Stoll | 324/9 |
| 3,753,110 | 8/1973 | Ikeda et al. | 324/182 |
| 3,893,026 | 7/1975 | Glazkov et al. | 324/72 |

OTHER PUBLICATIONS

"Electrolytic Corrosion—Soil Corrosion Handbook," (Japanese), Institute of Electrical Engineering, (1966).
F. A. Champion, "Corrosion Testing Procedures," Second Edition, Wiley, N.Y. 1965, pp. 309–315.
L. L. Shrein, Editor, "Corrosion," Newnes, Ltd., London, 1963, pp. 11.45–11.49.
K. G. Compton, "Corrosion," vol. 14, 237t–244t, (1958).
H. Uhlig, "Corrosion & Corrosion Control," Second Edition, Wiley, N.Y., 1971, pp. 206–211.

Primary Examiner—G. L. Kaplan
Assistant Examiner—Aaron Weisstuch
Attorney, Agent, or Firm—Staas & Halsey

[57] ABSTRACT

An electrolytic corrosion measuring apparatus comprising a first terminal to be connected to an electric conductor, such as a rail of electric railways, water pipe, gas pipe, telephone cable, power cable or the like, installed in electrical contact with the earth and a second terminal to be connected to an earthed reference electrode; a solid state electrochemical potential memory device which exhibits a terminal voltage between an anode and a cathode linearly changing as a function of the charging or discharging quantity of electricity fed to the device and which is capable of holding the terminal voltage, said device being connected to the terminals to receive an input therefrom; an amplifier for amplifying the terminal voltage of the device; and a meter for displaying the output of the amplifier. A preferred embodiment of the present invention comprises two sets of such memory device, amplifier and meter: one being for a positive going component of the input and the other for a negative component. The value indicated by the meter is associated with an amount of electrolytic corrosion occurring in the conductor during a time period when the apparatus is connected to the conductor and the earth, and thus affords a qualitative measurement indication of the amount of electrolytic corrosion so occurring.

14 Claims, 11 Drawing Figures

APPARATUS FOR MEASURING STRAY CURRENT ELECTROLYTIC CORROSION

This is a continuation of application Ser. No. 448,285, filed Mar. 5, 1974.

BACKGROUND OF THE INVENTION

1. Field of the Invention

The present invention relates to an apparatus for measuring electrolytic corrosion and providing a qualitative indication of the amount of electrolytic corrosion. More specifically the present invention relates to an apparatus for providing an indication associated with an amount of electrolytic corrosion which occurs in an electric conductor installed in contact with the earth.

2. Description of the Prior Art

In almost all electric railways, the electric cars are energized by a DC voltage source. Typically, a DC voltage is supplied between a supply line and a rail in view of the fact that the rail is a good electric conductor. The electric car is thus supplied with the electric power from a supply line and a rail, while the car moves along the rail. The fact that the rail is installed in contact with the earth, however, can cause an undesirable situation. More specifically, as is often the case with a city or town, other electric conductors, such as water pipes, gas pipes, telephone cables, power cables and the like, are installed in the earth, which can extend along and in the vicinity of the rails of the electric railways. Therefore, it can often occur that a portion of the power current of the electric railways flows through the earth and the adjacent other electric conductors by way of leakage. It has been well known that electric conductors, such as rails, pipes, cables or the like, installed in contact with the earth are corroded in an electrolytic manner, as a result of leakage current flowing from the conductor to the earth. Thus it is most important that those who maintain such electric conductors are aware of the tendency of such corrosion occuring in the conductor.

A typical prior art method of providing an indication associated with an amount of the corrosion occuring in an electric conductor installed in contact with the earth and thus a qualitative measurement of the amount of corrosion is as follows. A change in voltage as measured between the electric conductor and an earthed reference electrode installed in ideal, good electric contact with the earth is recorded on a record medium, such as a record sheet. The area of the waveform thus obtained is calculated, the area of the waveform being representative qualitatively of the quantity of electricity carried by the leakage current, which in turn is closely related to the amount of the corrosion. However, such a method is disadvantageous in that it is very tiresome and of low accuracy. Another prior art approach to measure qualitiatively the amount of corrosion comprises utilization of a silver or copper coulometer, in which the amount of silver or copper, and specifically the weight thereof deposited within the coulometer due to flow of leakage current caused by the conductor-to-earthed reference electrode potential indicates the leakage current, and thus the amount of corrosion. This approach is also of low accuracy. It is desired to provide an apparatus capable of measuring qualitatively with ease qualitative indication of the amount of electrolytic corrosion which occurs in an electric conductor installed in contact with the earth.

A voltage storing device of interest in connection with the present invention is disclosed in U.S. Pat. No. 3,753,110, issued Aug. 14, 1973 to Hironosuke Ikeda et al. and assigned to Sanyo Electric Co., Ltd. the same assignee as that of the present invention. As set forth in the referenced patent, Professor Takehiko Takahashi and Assistant Professor Osamu Yamamoto, Technological Department of Nagoya University, announced their study on the electrochemical potential memory device by the use of a solid state electrolyte at the 22nd annual assembly of Japan Chemical Association held on Apr. 5 to 7, 1969. Briefly stated, this device comprises an Ag electrode as a cathode, an Ag-Te alloy electrode as an anode, and a solid state electrolyte having high ion conductivity, such as $RbAg_4I_5$ sandwiched between both electrodes. When a DC voltage is applied to the device so that the Ag electrode may be negative, a portion of Ag contained in the Ag-Te alloy electrode migrates over to the Ag electrode, resulting in a decreased activity of Ag in the Ag-Te alloy, and thus an increased potential difference between both electrodes. The inventors of this device termed this state of operation as "charging". When the polarity of the applied DC voltage is reversed to that of the former case, Ag migrates back to And is refilled into the Ag-Te alloy resulting in the potential difference decreasing and returning to the initial value eventually. The inventors of this device termed this state of operation as "discharging". Study disclosed by the inventors of this device indicated that the electromotive force generated by the abovementioned charging or discharging current underwent linear change to some extent with respect to the charging or discharging quantity of electricity (current-time). Thus, this device makes it possible, as an outstanding characteristic, to do write-in and non-destructive read-out operations while preserving a relatively linear relation between the charging or discharging time and terminal voltage, and in addition, it can hold the memory condition for a relatively long period of time. These advantages mean that this device has potential use as an analog memory device. The referenced patent further discloses an improved electrochemical potential memory device. More specifically, FIG. 6 of the referenced patent shows both an improved electrochemical potential memory device for eliminating the IR drop across the resistance of the electrolyte and the overvoltage caused by dissoluion or deposition of Ag, which improved device is basically characterized by the provision of an auxiliary cathode that comprises an output terminal for detecting the potential separately from the abovementioned cathode utilized as the input terminal for the current conduction.

In view of these advantageous characteristics of the abovementioned memory device, the present inventors recognized that it is possible to utilize this device as an essential component of an apparatus for measuring electrolytic corrosion by measuring the quantity of electricity related to the leakage current flowing from an electric conductor installed in contact with the earth. The present invention has thus been accomplished by the inventors in order that such possibility may be realized.

SUMMARY OF THE INVENTION

Briefly stated, the present invention comprises an electrolytic corrosion measuring apparatus comprising a solid state electrochemical potential memory device connected to an electric conductor installed in electrical contact with the earth and to an earthed reference electrode, and means for reading out the output voltage of the said potential memory device. The solid state electrochemical potential memory device exhibits a terminal voltage between an anode and a cathode linearly changing as a function of the charging or discharging quantity of electricity fed to the device, and is capable of holding the terminal voltage. The potential memory device is charged or discharged as a function of the leakage current flowing through the said electric conductor and, more specifically, as a function of the voltage potential developed between the aforesaid electric conductor and the earth electrode, which voltage is related to, in a qualitative manner, the leakage current and which voltage is supplied to the potential memory device to establish the charging or discharging thereof. Therefore, an output of the memory device as charged or discharged in a predetermined period of time is a function of qualitatively, the amount of electrolytic corrosion which is caused by the said leakage current.

In a preferred embodiment of the present invention, means responsive to the input leakage current for providing only one polarity component of the current to the potential memory device is provided, whereby only a positive or negative going component of the input leakage current is integrated by the memory device, thereby to provide a qualitative measure of the corrosion, in view of the fact that the positive going component of the leakage current is usually the primary cause of the electrolytic corrosion. In a further preferred embodiment of the present invention, two channels of the apparatus are provided, such that one of them is aimed to measure the integrated quantity of electricity caused by a positive going component of the leakage current, while the other is aimed to measure the integrated quantity of electricity caused by a negative going component of the leakage current. Separate measurement of the positive and negative going components of the leakage current is of assistance in the consideration of the electrolytic corrosion of the electric conductor.

Therefore, a principal object of the present invention is to provide an improved apparatus for measuring with precision and ease an amount of electrolytic corrosion which occurs in an electric conductor installed in electric contact with the earth.

An essential aspect of the present invention is to utilize a solid state electrochemical potential memory device for the purpose of qualitatively measuring an amount of electrolytic corrosion occuring in an electric conductor installed in electric contact with the earth.

Another aspect of the present invention is to charge or discharge a solid state electrochemical potential memory device as a function of either the positive going or the negative going component of the leakage current flowing through an electric conductor installed in electrical contact with the earth, whereby a qualitative measurement of the amount of electrolytic corrosion occuring in the electric conductor is provided in terms of an output voltage of the potential memory device.

These objects and other objects and features of the present invention will be better understood when taken in conjunction with the following detailed description made with reference to the accompanying drawings.

BRIEF DESCRIPTION OF THE DRAWINGS

In the drawings, like reference characters designate like portions.

DESCRIPTION OF THE PREFERRED EMBODIMENTS

As described in the foregoing section of Description of the Prior Art, the present invention utilizes the prior art electrochemical potential memory device including a solid state electrolyte. As described already, this device has a significant characteristic in that the terminal voltage or electromotive force of the device changes in an approximately linear relation to the charging or discharging quantity of electricity flowing therethrough. Accordingly, prior to a detailed description of the present invention, it would be appropriate to give a more detailed description of such an electrochemical potential memory device.

Figure 1:
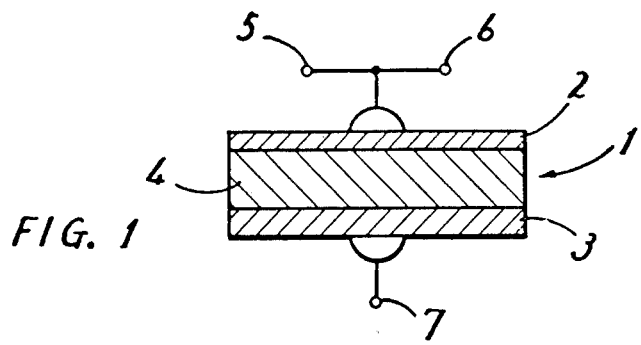
FIG. 1 illustrates a schematic sectional view of an electrochemical potential memory device to be used in the apparatus of the present invention.

FIG. 1 illustrates a schematic sectional view of an electrochemical potential memory device 1 which is used in the apparatus of the present invention. It may be considered that this device is a kind of cell which comprises a solid state electrolyte 4 of high ion conductivity, such as $RbAg_4I_5$ or $Ag_3SI$, sandwiched between a cathode 2 mainly including silver (Ag) and an anode 3 mainly including an alloy of silver and a member selected from the group consisting of sulfur (S), selenium (Se) and tellurium (Te), preferably an Ag-Te alloy. When a DC voltage is applied between electrodes 2 and 3 of this device 1 through an input terminal 5 and a common terminal 7, respectively, in such a way that the anode 3 of this device may be positive and the cathode 2 may be negative, silver contained in the Ag-Te alloy in the anode 3 is ionized and dissolved into the solid state electrolyte 4 and is deposited on the cathode 2. In this specification, such a state of operation is referred to as "charging" hereinafter. When a DC voltage is applied to the abovementioned device in the directly opposite polarity to the above case, silver deposited over the cathode 2 migrates onto the anode 3 and is deposited thereupon. In this specification, such a state of operation is referred to as "discharging" hereinafter.

Figure 2:
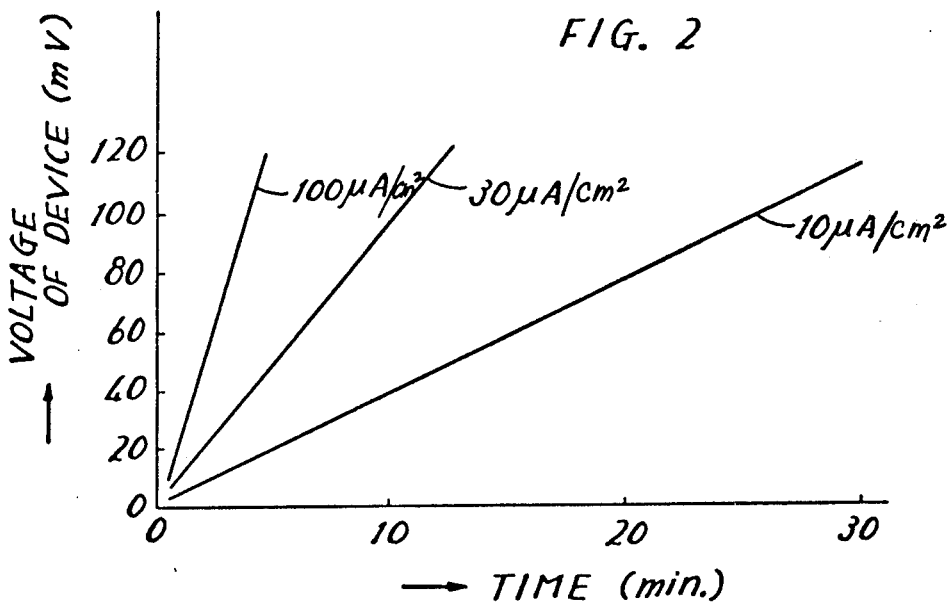
FIG. 2 is a graph which indicates a relation between the charging or discharging time, and thus the quantity of electricity, and the electromotive force of the FIG. 1 device, by taking the current for charging or discharging the device as a parameter.

FIG. 2 is a graph which indicates the relation between the charging or discharging time, and thus the quantity of electricity, and the electromotive force of the abovementioned device, as detected between the electrodes 2 and 3 through an output terminal 6 and the common terminal 7, respectively, by taking the current for charging or discharging the device as a parameter. FIG. 2 illustrates the following functions and characteristics of such a device: the value of the electromotive force of this device as a cell is dependent upon the activity of silver contained in the Ag-Te alloy of cathode 3, the activity of the silver varies to rather substantially in response to any slight charging or discharging operation, or current flow when the atomic composition ratio of silver and tellurium contained in the Ag-Te alloy approximates to a value of 2, and the relation between the abovementioned electromotive force and the charging or discharging quantity of electricity $i \cdot t$, where $i$ is a current value and $t$ is time, generally is linear during the charging or discharging period where the electromotive force is of a relatively low voltage range (from 0(zero) to 100mV. as per the embodiment illustrated in FIG. 2) and also where the current density is of a relatively low order (less than $100\mu A/cm^2$ as per the embodiment illustrated in FIG. 2). In this connection, it is to be pointed out that the application of a given voltage to the device in either a charging or discharging manner causes a substantially constant current to flow therethrough and therefore the said linear relation also is demonstrated between the terminal voltage of the device and the charging or discharging time.

It has further been known that this device has an additional characteristic of being capable of holding the potential as established immediately before cutting off the current, even after the cutting off of the current supplied to this device for the abovementioned voltage range (from 0(zero) to 100mV. as per the embodiment illustrated in FIG. 2).

Accordingly, the present invention is directed to providing an apparatus for qualitatively measuring an amount of electrolytic corrosion which occurs in an electric conductor installed in electrical contact with the earth, in which such an amount is determined in terms of the output voltage of the potential memory device produced in response to a current associated with the leakage current supplied thereto and which occurs in such an electric conductor, and specifically, wherein that current is caused to flow in the potential memory device in accordance with a voltage produced between the electric conductor and the reference or earth potential causing the leakage current, which potential is supplied to the potential memory device.

It is understood that the embodiment described with reference to FIG. 1 includes terminals 5 and 6 connected in common to a single cathode 2 by means of which the charging or discharging current is supplied and also the terminal voltage of the device is detected. In this connection it is recalled that the device shown in FIG. 1 can be considered as a cell, as mentioned previously. Therefore, in case of such a device having a common cathode for supply of the current and for detection of the terminal voltage, the detected output voltage is sum of an electromotive force of the device and of an overvoltage of the device as a cell. This results from the fact that the start or the stop of the electric current conduction into the device causes an overvoltage to be superposed on the detected voltage and therefore the output voltages detected at the device 1 immediately before and after the change of electrical current conduction state are different. This means that the voltage holding characteristic of the device is degraded. It has been found that the said degradation of the voltage holding characteristic is aggravated by the fact that an increased current for charging and discharging the device causes a greater overvoltage, resulting in more inaccurate measurement. Thus it is desired to provide an improved potential memory device that eliminates the abovementioned problem.

The overvoltage as occurs in the electrochemical potential memory device causing a voltage drop after the cutting off of the current conduction into the device may be classified as follows:

1. A voltage drop caused by the current flowing through the resistance involved in the solid state electrolyte of the device (or an IR drop across the resistance in the electrolyte).

2. An overvoltage caused by dissolution or deposition of Ag at an interface between the electrolyte and the anode or cathode.

3. An overvoltage caused by diffusion of Ag ion into the anode.

Figure 3:
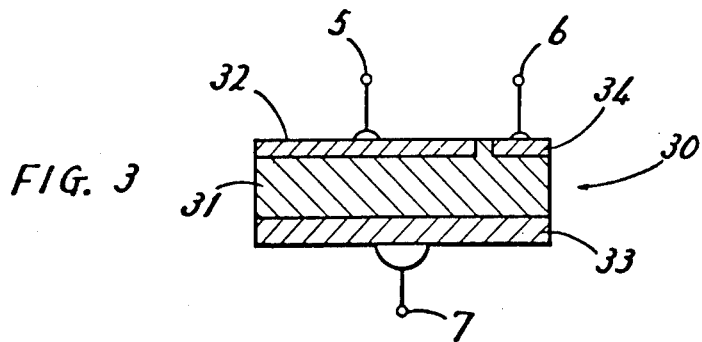
FIG. 3 shows a schematic sectional view of an improved electrochemical potential memory device for eliminating the IR drop across the resistance in the electrolyte and the overvoltage caused by dissolution or deposition of Ag.

FIG. 3 shows a schematic sectional view of an improved electrochemical potential memory device 30 for eliminating the IR drop across the resistance in the electrolyte as described in the above subsection (1) and the overvoltage caused by dissolution or deposition of Ag as described in the above subsection (2). The device 30 shown in FIG. 3 is basically characterized by the provision of an auxiliary cathode 34 that comprises an output terminal 6 for detecting the potential separately from the above-mentioned cathode 32 available for the input terminal 5 for the current conduction. More specifically, the device shown in FIG. 3 esssentially comprises a solid state electrolyte 31 composed of $Ag_3SI$, an anode 33 composed of an Ag-Te alloy, a cathode 32 composed of Ag, and an auxiliary cathode 34 composed also of Ag.

Figure 4:
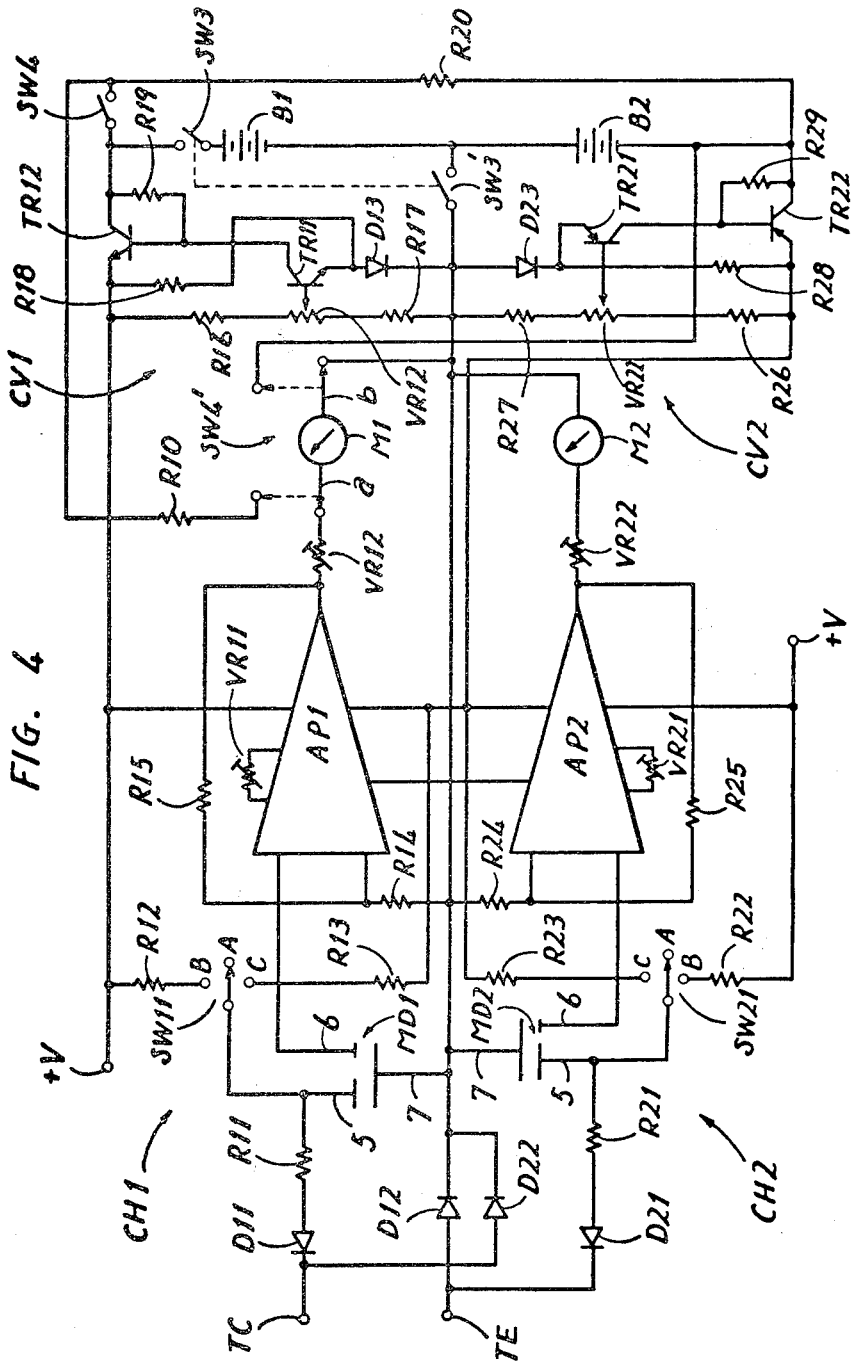
FIG. 4 illustrates a schematic diagram of an electrolytic corrosion measuring apparatus embodying the present invention using the abovementioned potential memory device.

FIG. 4 illustrates a schematic diagram of an electrolytic corrosion measuring apparatus embodying the present invention using the abovementioned potential memory device. The apparatus shown comprises a terminal TC to be connected to an electric conductor installed in contact with the earth, such as a rail, water pipe, gas pipe, telephone cable, power cable, or the like, and another terminal TE to be connected to an earthed reference electrode (not shown) prepared to be in good electrical contact with the earth, for the purpose of measurement of the present invention. Connection is made from the terminal TE through a diode D12, from an anode 7 to a main cathode 5 of the potential memory device MD1, and through a resistor R11 and a diode D11 to the terminal TC, the diodes D12 and D11 being in a forward direction as to the direction of the abovementioned order. Likewise, connection is made from the terminal TC through a diode D22, from an anode 7 to a main cathode 5 of a potential memory device MD2, and through a resistor R21 and a diode D21 to the terminal TE, the diodes D22 and D21 being in a forward direction as to the direction of the abovementioned order. The main cathodes 5 of the potential memory devices MD1 and MD2 are connected to the movable contacts of the switches SW11 and SW21, respectively. The contacts B of the switches SW11 and SW21 are connected through resistors R12 and R22, respectively, to a positive voltage terminal V, and the contacts C of the switches SW11 and SW21 are connected through resistors R13 and R23, respectively, to a negative voltage terminal, while the contacts A of the switches SW11 and SW21 remain unconnected. Auxiliary cathodes 6 of the potential memory devices MD1 and MD2 are connected to corresponding input terminals of direct current amplifiers AP1 and AP2, respectively. Resistors R14 and R15 are connected to the other input of the amplifier AP1 and resistors R24 and R25 are connected to the other input of the amplifier AP2. Variable resistors VR11 and VR21 are provided for the purpose of offsetting adjustment of the amplifiers AP1 and AP2, respectively. The outputs of the amplfiers AP1 and AP2 are applied through variable resistors VR12 and VR22 to meters M1 and M2, respectively, such that full scale adjustment of the respective meters M1 and M2 can be made by varying the variable resistors VR12 and VR22, respectively.

As seen from the foregoing description, it is seen that the apparatus shown comprises a pair of channels CH1 and CH2 for processing the electrical signal, one for a positive going component of the signal and the other for a negative going component of the signal, as to be more fully described hereinafter. In order to energize these two channels CH1 and CH2 individually, the apparatus shown further comprises a pair of respective power sources. More specifically, the channel CH1 including the potential memory device MD1, the amplifier AP1 and the meter M1 is supplied with electric power through a constant voltage circuit CV1 from a battery B1. The constant voltage circuit CV1 comprises transistors TR11 and TR12, a diode D13, resistors R16, R17, R18, and R19 and a variable resistor VR12, which are connected in a well known manner. Similarly, the channel CH2 including the potential memory device MD2, the amplifier AP2 and the meter M2 is supplied with electric power through a constant voltage circuit CV2 from a battery B2. The constant voltage circuit CV2 comprises transistors TR21 and TR22, diode D23, resistors R26, R27, R28 and R29 and a variable resistor VR22, which are connected in the same manner. The constant voltage circuit of such a connection and operation thereof are well known to those skilled in the art. The apparatus shown further comprises a pair of power switches SW3 and SW3', ganged with each other and connected as shown, resistors R10 and R20 and a switch SW4 and ganged switch SW4', the latter for the purpose of checking the batteries B2 and B1, as to be more fully described hereinafter.

Figure 5:
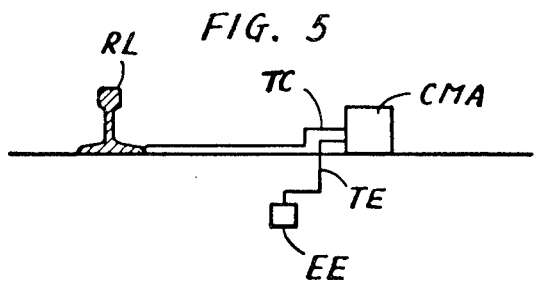
FIG. 5 shows an example of the environments in which the present invention is advantageously utilized.

FIG. 5 shows an example of the environments in which the present invention is advantageously utilized. More specifically, the inventive apparatus is shown for qualitatively measuring an amount of electrolytic corrosion occuring in a rail RL of the electric railways. The terminal TC of the inventive apparatus CMA, as shown in FIG. 4, is connected to the rail RL and the terminal TE of the apparatus CMA is connected to an earthed reference electrode EE installed in good contact with the earth.

In operation, first the power switches SW3 and SW3' are turned on, so that all the circuits in the apparatus are in an energized condition. By using the switches SW11 and SW21, initial adjustment of the meters M1 and M2, and thus of the potential memory devices MD1 and MD2 is made. If the meters M1 and/or M2 indicate that the devices MD1 and/or MD2 have been precharged, then the corresponding switches SW11 and/or SW21 are turned to their contacts B, until a discharging current flowing through the resistors R12 and/or R22 discharges the devices MD1 and/or MD2 to an initial condition, at which time switches SW11 and/or SW21 are returned to the contacts A. Similarly, if the meters M1 and/or M2 indicate that the devices MD1 and/or MD2 have been predischarged as compared with the initial condition, then the switches SW11 and/or SW21 are turned to their contacts C until a charging current flowing through the resistors R13 and/or R23 charges the devices MD1 and/or MD2 to an initial condition, at which time the switches SW11 and/or SW21 are returned to the contacts A. In order to check the batteries B2 and B1, the switch SW4 is closed, which is ganged with the switch SW4', so that contacts $a$ and $b$ thereof are switched to the terminals $a'$ and $b'$, so as to form a closed circuit including the switch SW4, the resistor R10, the meter M1, the batteries B2 and B1 in series and the switch SW3, with the batteries B2 and B1 shunted by the resistor R20. As a result, the meter M1 indicates the capacity of the batteries B2 and B1.

Figure 6:
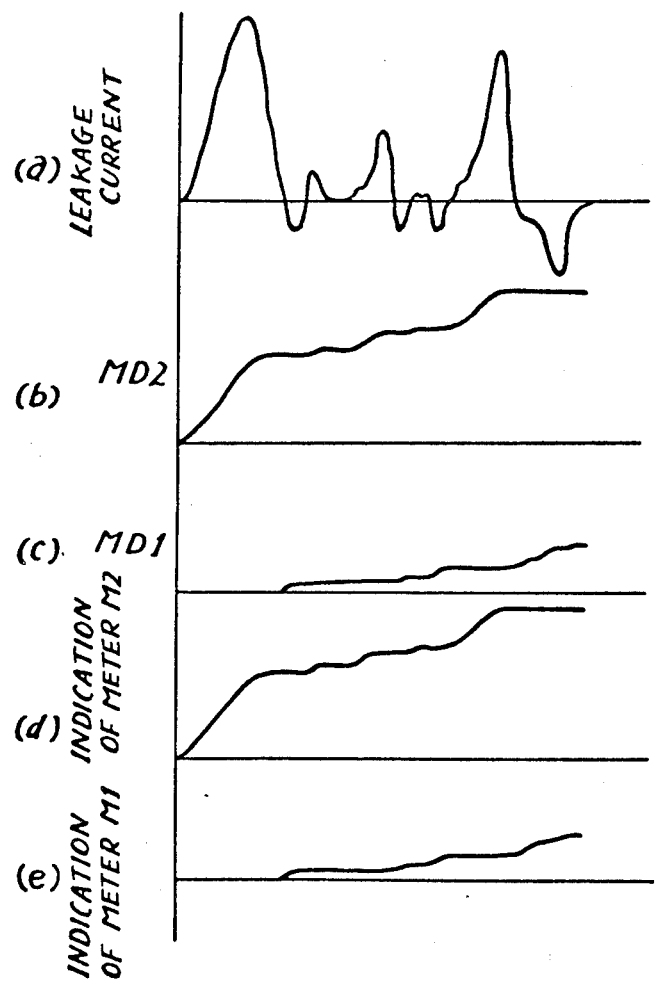
FIG. 6 shows waveforms of electric signals at various portions of the FIG. 4 apparatus.

FIG. 6 ($a$) shows a typical example of a waveform of the leakage current flowing from a rail of an electric railway. The apparatus shown in FIG. 4 and connected as shown in FIG. 5 is thus supplied with a current developed in accordance with the potential existing between the terminals TC and TE which potential results in leakage current. Of the leakage current of such waveform, only a positive going component of the aforenoted current produced in accordance with the voltage across terminals TC and TE; flows from the terminal TC through the diode D22, device MD2 from the anode to the main cathode thereof, the resistor R21 and the diode D21 to the terminal TE, so that the device MD2 is charged as a function of the quantity of electricity of the aforenoted current so produced and flowing therethrough. An output from the device MD2 is applied to the amplifier AP2 and is amplified thereby, so that the amplified output drives the meter M2 to indicate an integrated value of the positive going component of the aforenoted current produced in accordance with the voltage across terminals TC and TE, which voltage results in the leakage current. Similarly, only a negative going component current flows from the terminal TE through the diode D12, the device MD1 from the anode to the main cathode thereof, the resistor R11 and the diode D11 to the terminal TC, so that the device MD1 is charged as a function of the quantity of electricity flowing therethrough. An output from the device MD1 is applied to the amplifier AP1 and is amplified thereby, so that the amplified output drives the meter M1 to indicate an integrated value of the negative going component of the aforenoted current produced by the voltage between terminals TC and TE, resulting from the leakage current. The curves (b) and (c) of FIG. 6 show a change of the outputs from the devices MD2 and MD1, respectively, and the curves (d) and (e) of FIG. 6 show the corresponding changes of the indications by the meters M2 and M1, respectively. Thus, it is seen that the apparatus of the embodiment shown in FIG. 4 individually indicates the integrated values of each of the positive and negative components of the aforenoted current produced as a result of the voltage across terminals TC and TE, which voltage results in the leakage current flowing from and to the electric conductor through the earth respectively. It has been observed that such currents afford a qualitative indication of the amount of electrolytic corrosion occuring in the electric conductor installed in contact with the earth due to the leakage current flowing therefrom. Thus the present invention makes it possible to measure qualitatively the amount of such electrolytic corrosion of the electric conductor with ease and accuracy.

As a result of actual measurement of corrosion which occurs in various electric conductors installed in contact with the earth, it has been observed that a relatively large leakage current flows therefrom in case of rails of the electric railways, whereas a very small leakage current flows therefrom in case of water pipes, gas pipes, telephone cables, power cables, or the like. Therefore, the apparatus as shown in FIG. 4 is less advantageous for use in measuring the corrosion caused by the abovementioned small leakage current, in view of the fact that the forward drop across the diodes D11, D12, D21 and D22 results in introducing an error in the measured value of corrosion.

Figure 7:
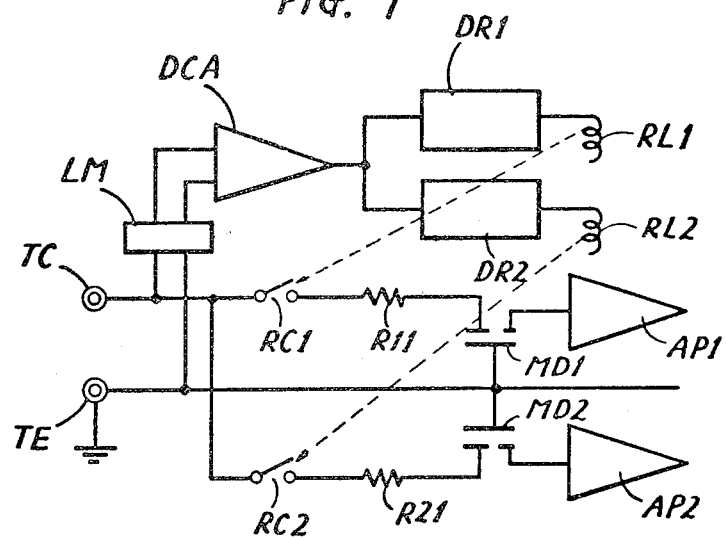
FIG. 7 illustrates a block diagram of a preferred embodiment of the inventive apparatus capable of qualitatively measuring the corrosion with high precision.

Fig. 7 illustrates a block diagram of a preferred embodiment of the inventive apparatus particularly capable of measuring the quantity of the aforenoted current flow produced as a result of the potential difference between the terminals, as above noted, and which results in the leakage current with high precision, and thus is suited for qualitative measurement of the corrosion caused by such a small leakage current. It is pointed out that FIG. 7 shows only a portion of the apparatus from the terminals TC and TE to the amplifiers AP1 and AP2 in terms of the reference characters used in FIG. 4. Briefly described, as compared with the FIG. 4 apparatus, the FIG. 7 apparatus comprises relay contacts RC1 and RC2, in lieu of the switching diodes D11 and D12, and D21 and D22, respectively, which relay contacts RC1 and RC2 are controlled by relay coils RL1 and RL2, respectively, which are connected to drivers DR1 and DR2, respectively. The drivers DR1 and DR2 are supplied with an input signal representative of polarity of the leakage current from direct current amplifier DCA, which receives the voltage and hence the current flow produced as a result of the leakage current, from the terminals TC and TE through a limiter LM.

In operation, a positive going component of the current produced as a result of the voltage between the terminals TC and TE, is first amplitude-limited by the limiter LM and is applied to the direct current amplifier DCA, where an output representative of the positive polarity is obtained to drive the driver DR1, so that the relay coil RL1 is energized and accordingly the relay contact RC1 is closed, with the result that only the potential memory device MD1 is discharged as a function of the said positive going current. Quite similarly a negative going component of the aforenoted current drives only the driver DR2 and thus only the relay coil RL2 is energized, so that the contact RC2 is closed and only the potential memory device MD2 is charged as a function of the said negative going current.

Figure 8:
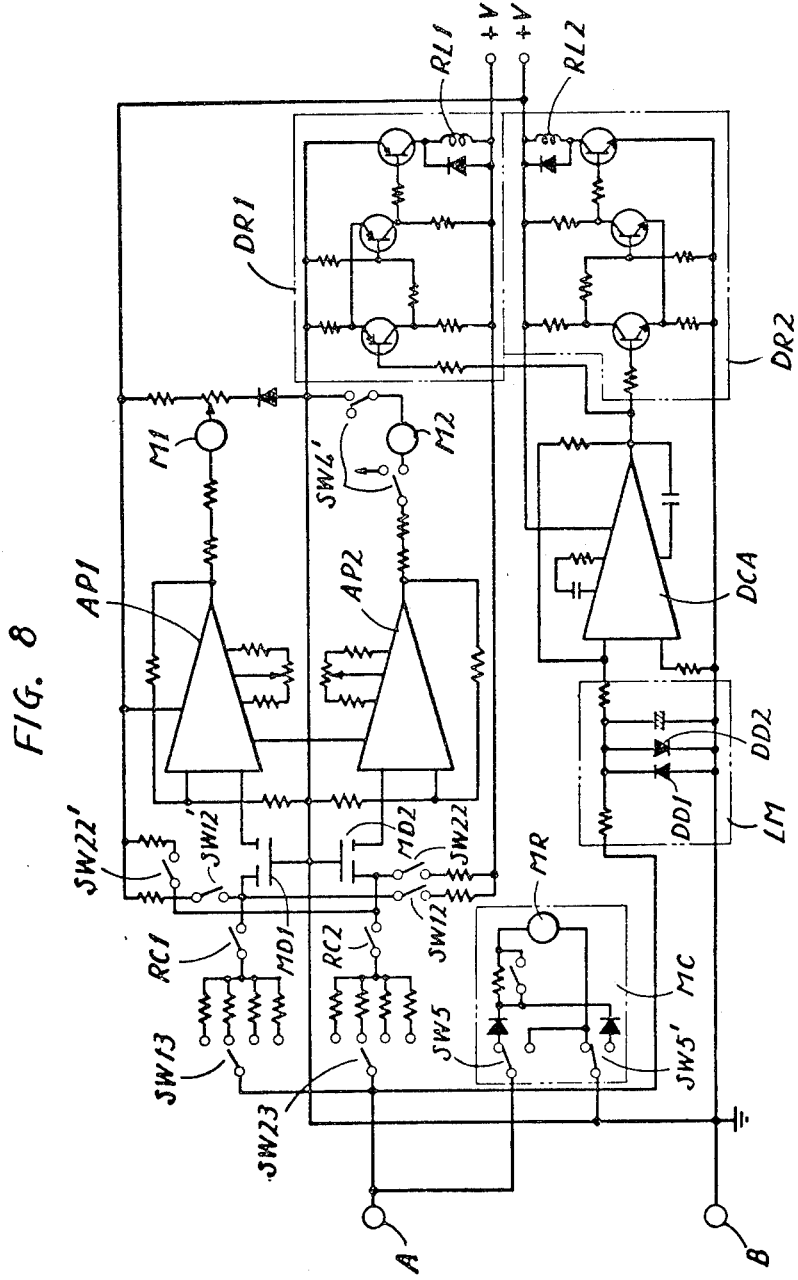
FIG. 8 illustrates a schematic diagram of an apparatus similar to that of FIG. 4 but employing the FIG. 7 embodiment.

FIG. 8 illustrates a schematic diagram of an apparatus similar to that of FIG. 4 but employing the FIG. 7 embodiment. The limiter comprises a pair of diodes DD1 and DD2, connected in a direction opposite to each other and in parallel to the input of the amplifier DCA. The diode DD2 provides thereat an amplitude-limited output by way of a forward drop thereacross in response to the positive going input. On the other hand, the diode DD1 provides thereat an amplitude-limited output by way of a forward drop thereacross in response to the negative going input. Accordingly, the amplifier DCA provides an amplified output representative of the positive or negative going component in response to the output from the limiter LM. The output from the amplifier DCA, as amplified and inverted thereby in response to the positive going input, is wave-shaped by the driver DR1, which comprises a well-known Schmidt circuit comprising transistors and resistors connected as shown in the figure, an output of which is connected to the relay coil RL1. Likewise, the output from the amplifier DCA, as amplified and inverted thereby in response to the negative going input, is wave-shaped by the driver DR2, which comprises a corresponding Schmidt circuit, an output of which is connected to the relay coil RL2.

In comparison with the FIG. 4 apparatus, the FIG. 8 apparatus additionally comprises a pair of switches SW13 and SW23, each corresponding to the amplifiers AP1 and AP2, respectively, for changing the input impedance to the potential memory device MD1 and MD2, respectively, and thus for changing or adjusting the full scale range of the meters M1 and M2, respectively, in a manner well known to those skilled in the art. The FIG. 8 apparatus further comprises a monitor circuit MC for monitoring an instantaneous value of the input leakage current, as regards the positive going component and the negative going component individually, by turning ganged switches SW5 and SW5' to the contacts A and B, respectively. The positive going and negative going components of the input leakage current are monitored by the meter MR by turning the ganged switches SW5 and SW5' to the contacts A and B, respectively. For the purpose of initial adjustment of the potential memory devices MD1 and/or MD2, a switch SW12 ot SW12' is closed to forcibly charge or discharge, respectively the device MD1, and/or switches SW22 or SW22' is closed to forcibly charge or discharge, respectively, the device MD2. Other portions of the FIG. 8 apparatus are substantially the same as those of the FIG. 4 apparatus and therefore a further description thereof will be omitted.

Figure 9:
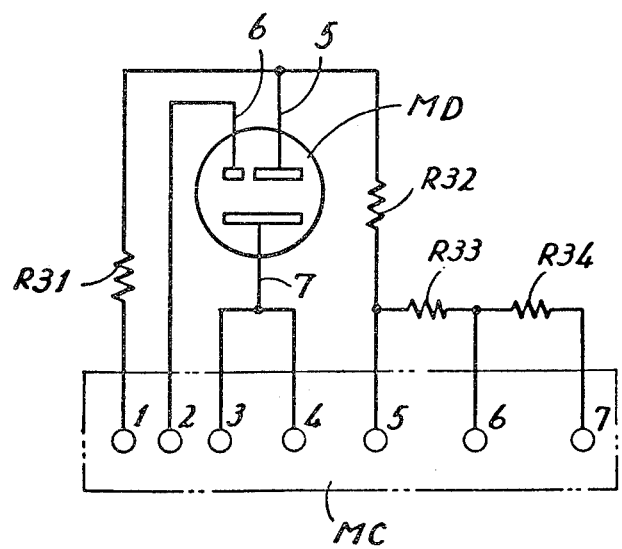
FIG. 9 illustrates a schematic diagram of a module incorporating a potential memory device together with some resistors connected in association therewith.

FIG. 9 illustrates a schematic diagram of a module in which the potential memory device of the FIGS. 4 or 8 apparatus has been incorporated together with some resistors associated therewith. The FIG. 9 module comprises the potential memory device MD and a multi-connector socket MC, terminals 1, 2, 3, 4, 5, 6, and 7 which are connected to the anode 7, main cathode 5 and auxiliary cathode 6 of the device together with resistors R31, R32, R33 and R34, as shown in FIG. 9. According to a preferred embodiment of the present invention a multiplicity of the FIG. 9 modules are prepared for the purpose of distributing them at predetermined intervals along the electric conductor, the corrosion of which is to be measured, so that the aforenoted current flowing as a result of the potential developed across the aforenoted terminals and producing the leakage current from the conductor can be measured at a multiplicity of positions at the same time. Such setting is done by connecting the terminals 4 and 5, 6 or 7 to the conductor and the earth electrode. After a predetermined period of time of measurement by the use of these modules, the modules are gathered and the charged quantity of electricity is measured by a reading device.

Figure 10:
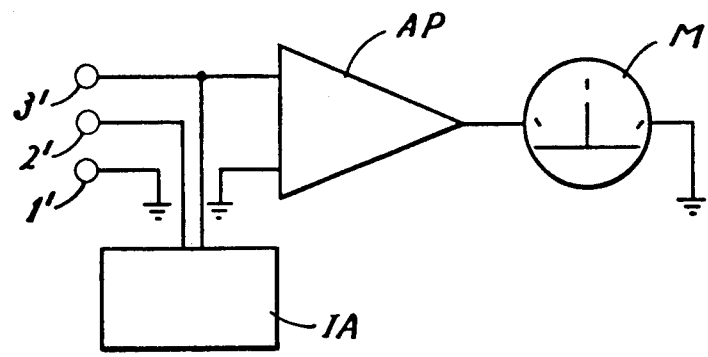
FIG. 10 illustrates a block diagram of a reading device suited for reading out the stored quantity of electricity of the potential memory device of the FIG. 9 module.

FIG. 10 illustrates a block diagram of a reading device suited for reading out the stored quantity of electricity of the potential memory device of the FIG. 9 module and thus the output of the potential memory device of the FIG. 9 module. For the purpose of reading out the output of the memory device, terminals 1', 2' and 3' of the reading device are connected to the terminals 1, 2 and 3, respectively, of the FIG. 9 module. The reading device comprises an amplifier AP and a meter M, which may be substantially the same as those described in the FIGS. 4 and 8 apparatus. The reading device shown further comprises an initial adjustment circuit IA, which may be substantially the same as that described in the FIGS. 4 and 8 apparatus.

Figure 11:
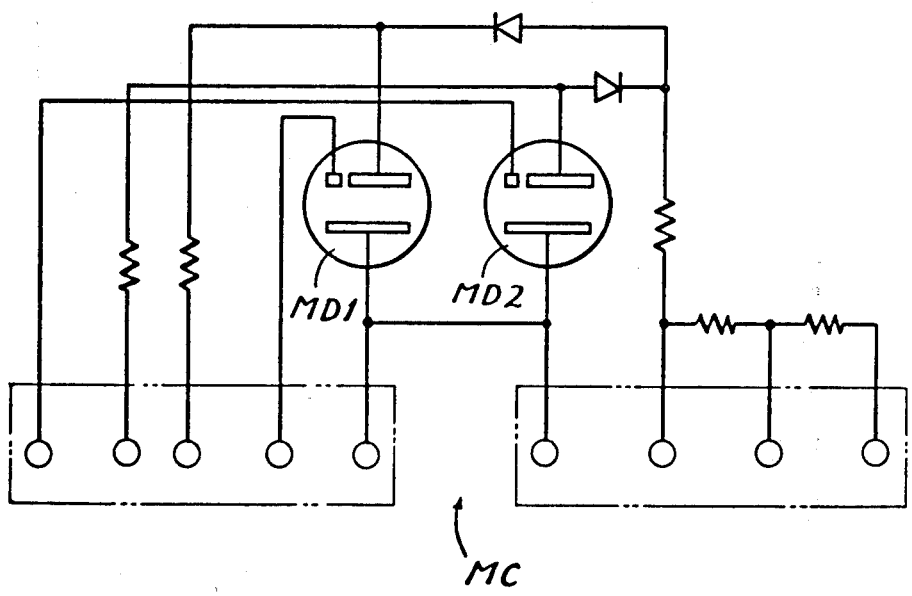
FIG. 11 illustrates a schmatic diagram of another embodiment of the potential memory device module.

FIG. 11 illustrates a schematic diagram of another embodiment of the potential memory device module. In comparison with the FIG. 9 module, the FIG. 11 module comprises a pair of potential memory devices MD1 and MD2 and a multiconnector, terminals of which are connected to the memory devices together with some resistors and diodes associated therewith. The FIG. 11 module is more advantageous in that the positive and negative going components of the aforenoted current flowing as a result of the leakage current can be measured using a single module.

Apparatus constructed in accordance with the invention is commercially available and is marketed by Sanyo Electric Company Ltd. of Osaka, Japan. Such apparatus available from this company is identified as an "Electrolytic Corrosion Meter" and one type marketed by Sanyo has a rated time range of 24 hours and an input signal voltage range of 0.5 – 150 volts.

While specific preferred embodiments of the invention have been described, it will be apparent that obvious variations and modifications of the invention will occur to those of ordinary skill in the art from a consideration of the foregoing description. It is therefore desired that the present invention be limited only by the appended claims.

What is claimed is:

1. An apparatus for qualitatively measuring an amount of electrolytic corrosion which occurs in an electric conductor installed in electrical contact with the earth due to leakage current flowing between said electric conductor and the earth resulting from a corrosion potential therebetween, comprising:

an earthable reference electrode adapted to be disposed in good electrical contact with the earth,
   a solid state electrochemical memory device comprising:
      a cathode including an active metal,
      an anode comprising an alloy including said metal, and
      a solid state electrolyte having ion conductivity sandwiched between said cathode and said anode,
   said potential memory device exhibiting a terminal voltage between said anode and said cathode substantially linearly changing as a function of the charging or discharging quantity of electricity supplied to said device in accordance with the anode being positive or negative, respectively,
   means for connecting said potential memory device to said electric conductor and to said earthable reference electrode for receiving therefrom a current flow which is produced as a result of the corrosion potential therebetween causing said leakage current, and which may vary in direction of flow corresponding to the polarity of said corrison potential, and for conveying said current flow to said potential memory device so as to effect a linear change of said terminal voltage, and,
   output means connected to said potential memory device for providing a qualitative indication of the amount of electrolytic corrosion occurring in said electric conductor in terms of the terminal voltage of said potential memory device,
   said apparatus further including a selecting means, disposed between said connecting means and said device, for automatically selecting that current flow having a direction corresponding to a preselected polarity of said corrosion potential, whereby to cause said output means to provide said qualitative indication of the amount of electrolytic corrosion due to leakage current flowing in said direction corresponding to said preselected polarity.

2. The electrolytic corrosion measuring apparatus in accordance with claim 1, in which said cathode comprises
   a main cathode including an active metal connected to receive said current flow, and
   an auxiliary cathode including an active metal connected to said output means for providing the qualitative indication of the electrolytic corrosion occurring in said electric conductor.

3. The electrolytic corrosion measuring apparatus in accordance with claim 1, in which the cathode of said device includes Ag and the anode thereof includes an alloy of Ag and a chalcogen element.

4. The electrolytic corrosion measuring apparatus in accordance with claim 1, in which there is further provided a second selecting means for selecting that current flow having a direction corresponding to a polarity of said corrosion potential opposite to said preselected polarity, and
   a second potential memory device connected to said second selecting means for receiving said current flow having a direction corresponding to said polarity of said corrosion potential opposite to said preselected polarity, and including
   second output means connected to the second memory device for providing a qualitative indication of the amount of electrolytic corrosion occurring in said electric conductor due to leakage current flowing in that direction corresponding to said polarity opposite to said preselected polarity.

5. The electrolytic corrosion measuring apparatus in accordance with claim 4 wherein said means for connecting said potential memory device to said electric conductor and to said electrode includes:

switching means selectively operable to supply said one polarity component of said produced current flow to said first potential memory device and said opposite polarity component of said produced current flow to said second potential memory device, and wherein there is further provided.

means connected between said electric conductor and said electrode for detecting the polarity of leakage current and operatively associated with said switching means for correspondingly actuating said switching means.

6. The electrolytic corrosion measuring apparatus as recited in claim 5 wherein:
said switching means comprises first and second contacts associated, respectively, with said first and second potential memory device, and wherein
said means for detecting the polarity of the leakage current comprises:
a limiter connected to said electric conductor and to said electrode for receiving the said current flow produced in response to the leakage current,
a direct current amplifier connected to said limiter for receiving the output of said limiter and for producing an amplified current output,
first and second driver circuits connected to said direct current amplifier and respectively responsive to the said one and said opposite polarity components of the amplified current output of said direct current amplifier for producing respective outputs, and
first and second relay coils connected respectively to said first and second driver circuits and to said switching means, and respectively energized by the outputs of said first and second driver circuits to correspondingly and selectively actuate the respectively associated contacts.

7. The electrolytic corrosion measuring apparatus in accordance with claim 1, in which said selecting means comprises a unidirectionally conducting device.

8. The electrolytic corrosion measuring apparatus in accordance with claim 1, which further comprises
means for selectively and forcibly charging and discharging said potential memory device for initial adjustment of the memory device.

9. The electrolytic corrosion measuring apparatus in accordance with claim 1, in which said output means comprises
means connected to said electrochemical potential memory device for amplifying the terminal voltage of the memory device, and
means connected to said amplifying means for indicating an output of said amplifying means.

10. The electrolytic corrosion measuring apparatus in accordance with claim 1 wherein there is further provided:
switching means connected between said electrochemical potential memory device and said output means, having a normally open position, and having first and second closed positions for connection to opposite polarities of a reference voltage source, said switching means being selectively operable to said first and second positions for applying a first polarity reference voltage to said device to produce a charging current therethrough and alternatively a second, opposite polarity reference voltage to said device to produce a discharging current therethrough, and wherein said output means affords an indication of the terminal voltage of said memory device prior to supply of said produced current flow to said memory device for qualitative measurement of the corrosion, and
said switching means is operable to apply the appropriate polarity reference voltage to said memory device for producing a corresponding charging or discharging current through said memory device thereby to adjust the terminal voltage of the device to an initial value.

11. The electrolytic corrosion measuring apparatus in accordance with claim 10, wherein there is further provided:
power source means connected to said apparatus for providing power thereto,
second switching means operatively associated with said apparatus and said power source means for connecting said power source means to said apparatus for energization thereof, and
third switching means associated with said output indicating means, said third switching means normally connecting said indicating means to said memory device for indicating the terminal voltage thereof, and selectively operable for connecting said indicating means in circuit with said second switching means and said power source means for indicating the voltage level of the power source means.

12. In a system for qualitatively measuring the amount of electrolytic corrosion occurring in an electrical conductor installed in electrical contact with the earth as a function of leakage current flowing between said electric conductor and the earth resulting from a corrosion potential therebetween, the amount of which is to be measured qualitatively by a sensing device which is connected between said electric conductor and said earth so as to produce as an output a terminal voltage corresponding to an amount of current sensed by said sensing device and corresponding to said leakage current, the system including means connected to said sensing device for responding to the amount of current sensed by said sensing device for producing an output indication of the said amount of current sensed in terms of the terminal voltage of the said sensing device, an improved sensing device comprising:
a cathode including an active metal,
an anode comprising an alloy including said metal, and
a solid state electrolytic having ion conductivity sandwiched between said cathode and said anode, and wherein there is further provided
selecting means connecting said cathode and said anode of said device, on the one hand, to said electric conductor and said earth, on the other hand, for automatically selecting a current having a direction corresponding to a preselected polarity of said corrosion potential causing the leakage current, and for automatically inhibiting current having a direction corresponding to a polarity of said corrosion potential opposite to said preselected polarity, said device developing a terminal voltage between said anode and said cathode changing with time as a substantially linear function of the said supplied current, and said device being characterized by maintaining the developed terminal voltage during that time when said means last mentioned is automatically inhibiting supply of the said inhibited current.

13. A system as recited in claim 12, the improvement further comprising:
an additional sensing device, and
additional connecting means which includes means for automatically supplying current having a direction corresponding to a polarity of said corrosion potential opposite to said preselected polarity to said additional sensing device whereby the resulting terminal voltage of said additional device indicates qualitatively an amount of electrolytic corrosion occuring as a result of a leakage current corresponding to said corrosion potential of said opposite polarity.

14. A system as recited in claim 12, the improvement further comprising:
a module having a plurality of connecting terminals, said sensing device being included within said module and said anode and cathode thereof being connected to first corresponding ones of said connecting terminals, said first connecting terminals being adapted for connection to said electric conductor and to the earth, respectively, to receive the said produced current for application to said device, said anode and cathode thereof further being connected to second corresponding ones of said connecting terminals for readout of the terminal voltage of said potential memory device,
said module being adapted for independent connection at said first connecting terminals to said electric conductor and the earth for receiving therefrom said current produced as a result of said corrosion potential causing said leakage current for supply to said device for developing thereby a terminal voltage representative of the amount of electric corrosion, and being adapted for subsequent, independent connection at second connecting terminals thereof to the responding means of said system, said responding means responding to the terminal voltage of said device for producing a qualitative indication of the amount of the electrolytic corrosion.

* * * * *

UNITED STATES PATENT AND TRADEMARK OFFICE
CERTIFICATE OF CORRECTION

PATENT NO. : 4,003,815
DATED : January 18, 1977
INVENTOR(S) : Hironosuke Ikeda, Makoto Yamada, Hiroshi Kutsuyama It is certified that error appears in the above–identified patent and that said Letters Patent are hereby corrected as shown below:

Column 1, line 68, after "ease" insert --a--.
Column 14, line 51, "electrolytic" should be --electrolyte--.

Signed and Sealed this

Twelfth Day of April 1977

[SEAL]

Attest:

RUTH C. MASON
*Attesting Officer*

C. MARSHALL DANN
*Commissioner of Patents and Trademarks*